(12) United States Patent
Shimizu

(10) Patent No.: US 9,375,696 B2
(45) Date of Patent: Jun. 28, 2016

(54) MICROARRAY PROCESSING APPARATUS, WELL PLATE FOR MICROARRAY PROCESSING APPARATUS, MICROARRAY HOLDER, AND MICROARRAY WASHING METHOD

(71) Applicant: Mitsubishi Rayon Co., Ltd., Chiyoda-ku (JP)

(72) Inventor: Kouji Shimizu, Yokohama (JP)

(73) Assignee: Mitsubishi Rayon Co., Ltd., Chiyoda-ku (JP)

( * ) Notice: Subject to any disclaimer, the term of this patent is extended or adjusted under 35 U.S.C. 154(b) by 0 days.

(21) Appl. No.: 14/371,590

(22) PCT Filed: Apr. 4, 2013

(86) PCT No.: PCT/JP2013/060336
§ 371 (c)(1),
(2) Date: Jul. 10, 2014

(87) PCT Pub. No.: WO2013/151135
PCT Pub. Date: Oct. 10, 2013

(65) Prior Publication Data
US 2014/0364342 A1 Dec. 11, 2014

(30) Foreign Application Priority Data

Apr. 4, 2012 (JP) .................. 2012-085462
Apr. 4, 2012 (JP) .................. 2012-085463
Apr. 4, 2012 (JP) .................. 2012-085464

(51) Int. Cl.
*B01L 9/00* (2006.01)
*B01L 99/00* (2010.01)
*B01J 19/00* (2006.01)
*G01N 35/02* (2006.01)
*G01N 35/10* (2006.01)
*G01N 35/04* (2006.01)

(52) U.S. Cl.
CPC ............. *B01J 19/0046* (2013.01); *B01L 9/523* (2013.01); *G01N 35/028* (2013.01); *G01N 35/1011* (2013.01); *B01J 2219/00313* (2013.01); *B01J 2219/00373* (2013.01);
(Continued)

(58) Field of Classification Search
CPC ........... B01J 2219/00306; B01L 9/523; G01N 2035/0441; G01N 35/028
See application file for complete search history.

(56) References Cited

U.S. PATENT DOCUMENTS 6,500,388 B1 12/2002 Nagaoka et al.
2009/0205688 A1 8/2009 Ikushima

FOREIGN PATENT DOCUMENTS

JP 62 187852 11/1987
JP 10 048220 2/1998
(Continued)

OTHER PUBLICATIONS

International Search Report Issued Jun. 11, 2013 in PCT/JP13/060336 filed Apr. 4, 2013.

*Primary Examiner* — Paul Hyun
(74) *Attorney, Agent, or Firm* — Oblon, McClelland, Maier & Neustadt, L.L.P.

(57) ABSTRACT

Provided is a microarray processing apparatus which is capable of sufficiently washing a microarray. The microarray processing apparatus (30) includes a well plate (38) in which one or two or more wells (40) are formed, each well (40) accommodating a microarray (1), and a suction nozzle (46) that suctions a liquid from the well. The well has a concave portion whose upper end is opened, which has a depth equal to or greater than a height of the microarray, and into which a front end of the suction nozzle can be inserted up to a height position of a lower end of the microarray accommodated in the well. The suction nozzle can relatively descend in the well until the front end of the suction nozzle is located at the height position of the lower end of the microarray accommodated in the well.

12 Claims, 12 Drawing Sheets

(52) U.S. Cl.
CPC ............... *B01J 2219/00414* (2013.01); *B01J 2219/00533* (2013.01); *B01J 2219/00585* (2013.01); *G01N 2035/0437* (2013.01)

(56) References Cited

FOREIGN PATENT DOCUMENTS

| | | |
|---|---|---|
| JP | 11 094839 | 4/1999 |
| JP | 11 304821 | 11/1999 |
| JP | 2001 083158 | 3/2001 |
| JP | 2003 057245 | 2/2003 |
| JP | 2003 180329 | 7/2003 |
| JP | 2005 300291 | 10/2005 |
| JP | 2006 003349 | 1/2006 |
| JP | 2007 203196 | 8/2007 |
| JP | 2008 029244 | 2/2008 |
| JP | 2008 256643 | 10/2008 |
| JP | 2008 309669 | 12/2008 |
| WO | 2005 121745 | 12/2005 |

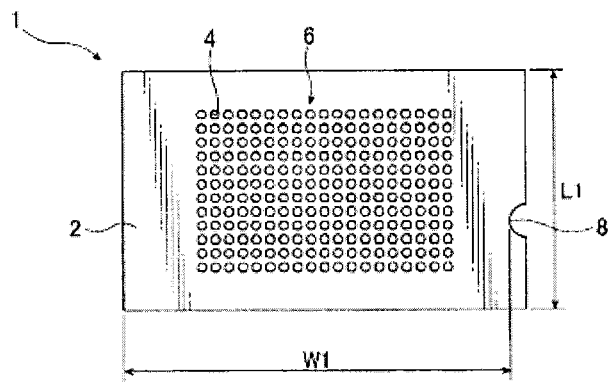
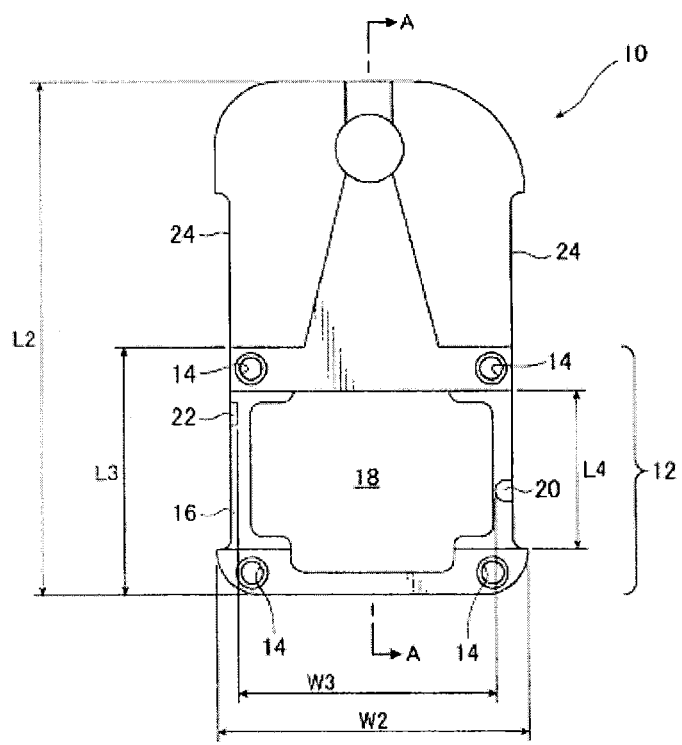

MICROARRAY PROCESSING APPARATUS, WELL PLATE FOR MICROARRAY PROCESSING APPARATUS, MICROARRAY HOLDER, AND MICROARRAY WASHING METHOD

TECHNICAL FIELD

The present invention relates to a microarray processing apparatus, a well plate for a microarray processing apparatus, a microarray holder, and a microarray washing method, and more particularly, to a microarray processing apparatus that performs a hybridization process and a washing process with respect to the microarray, and the like.

BACKGROUND ART

As a method of performing a collective expression analysis of a plurality of genes, an analysis method called a DNA chip method (DNA microarray method) is known. In this analysis method, a flat plate-shaped microarray in which for example, a plurality of DNA fragments are fixed inside through-holes at the central portion is immersed in a sample (liquid sample) containing expression genes and the like of a cell, which is marked by a fluorescent dye and the like and is a research target, to allow hybridization to be performed in order for complementary nucleic acids to be coupled, and a section in which a hybrid is formed is read by a detection device, thereby performing detection and quantity determination of the nucleic acids.

In the DNA chip method, when the hybridization is completed, before the detection and quantity determination of the nucleic acids, a washing process of washing a liquid sample adhering to the microarray with a wash buffer is performed.

In addition, in the DNA chip method, a microarray processing apparatus that performs the hybridization process and the washing process with respect to the microarray is used. In the microarray processing apparatus, a plurality of wells, which are formed in an elongated bottomed-hole shape having an upward opening, are arranged on an upper surface of the well plate. In each of the wells, a flat plate-shaped microarray, whose outer edge is held by a microarray holder having the same height as the depth of the well, is accommodated in an erected state, a liquid sample is injected into the well, and retention is performed for a predetermined time at a high temperature, thereby performing the hybridization process. Then, a wash buffer is injected into the well by using an injection nozzle while suctioning the liquid sample in the well, in which the microarray holder is accommodated, with a suction nozzle, thereby performing the washing process (Patent Document 1).

CITATION LIST

Patent Document

Patent Document 1: Japanese Unexamined Patent Application Publication No. 2008-309669

DISCLOSURE OF THE INVENTION

Problem to be Solved by the Invention

However, an amount of the liquid sample that is injected into the well when performing the hybridization is preferably as small as possible in consideration of reduction in burden on a patient from which the liquid sample is collected, and the like. Therefore, in the above-described microarray processing apparatus in the related art, a volume of the well is reduced by narrowing a gap between the microarray accommodated in the well in an erected state and an inner wall of the well, thereby decreasing a necessary amount of the liquid sample. As a result, in the microarray processing apparatus in the related art, the gap between the microarray accommodated in the well and the inner wall of the well is set to be smaller than the outer diameters of the suction nozzle and the injection nozzle.

On the other hand, with regard to the well, it is necessary to perform liquid suction by using the suction nozzle, and injection of a wash buffer and the like by using an injection nozzle. Therefore, a concave portion is formed in the well in order for the front ends of the suction nozzle and the injection nozzle to be inserted into the well in a state in which the microarray is accommodated in the well. The concave portion ends in a lateral portion of the microarray accommodated in the well to make the volume of the well as small as possible as described above. That is, in a process of washing the microarray, the suction nozzle can be inserted only to the lateral portion of the microarray, and thus it is difficult to suction the liquid inside the well before a liquid surface downwardly descends in relation to a lower end of the microarray accommodated in the well. As a result, it is difficult to sufficiently suction the liquid inside the well, and it is difficult for the wash buffer injected into the well to be widely spread up to the lower end of the microarray, and thus there is a possibility that washing of the microarray becomes not sufficient.

In addition, in the above-described microarray washing process in the related art, the wash buffer is injected into the well by using the injection nozzle while suctioning the liquid inside the well by using the suction nozzle, and thus it is difficult to sufficiently substitute the liquid sample and the wash buffer inside the well with each other. Therefore, there is a possibility that washing of the microarray becomes not sufficient.

In addition, the above-described microarray holder in the related art has a configuration in which a side end surface of the microarray, a surface that continues to the side end surface, and an outer edge portion of a rear surface are maintained in a lateral U-shaped. Therefore, in the hybridization process, a liquid sample, which penetrates between the side end surface of the microarray and the microarray holder, is not removed sufficiently even by the washing process using the wash buffer, and tends to remain. In addition, the liquid sample that remains as described above flows out during detection, and thus accuracy in detection and quantity determination of the nucleic acids may decrease.

In addition, it is necessary to hermetically seal the opening of each well to prevent the liquid sample injected into the well from being evaporated during performing the hybridization process. Therefore, in the microarray processing apparatus in the related art, the opening of the well is hermetically sealed with a well cover. Specifically, a flat plate-shaped well cover is disposed on an upper side of the well plate and a lower surface of the well cover faces an upper surface of the well plate. After injection of the liquid sample into the well in which the microarray is accommodated, the well cover is allowed to descend and the lower surface of the well cover is brought into close contact with the upper surface of the well plate, whereby the opening of the well is hermetically sealed with the lower surface of the well cover.

However, in the microarray processing apparatus in the related art, the height of the microarray holder that is accommodated in the well is the same as the depth of the well, and thus there is a possibility that an upper end surface of the microarray holder which is flush with an opening surface of the well may be suctioned onto the lower surface of the well cover. As a result, when ascending the well cover after completion of the hybridization process, there is a possibility that the microarray holder that is suctioned onto the lower surface of the well cover may be pulled up together with the well cover.

In addition, due to a manufacturing error of the well or the microarray holder, there is a possibility that the upper end surface of the microarray holder may upwardly protrude in relation to the opening surface of the well during accommodation into the well. As a result, the upper end surface of the microarray holder may come into first contact with the lower surface of the well cover in relation to the upper surface of the well plate during descending the well cover, and thus the opening of the well may not be hermetically sealed with the lower surface of the well cover.

The invention has been made to solve the above-described problem in the related art, and an object thereof is to provide a microarray processing apparatus which is capable of sufficiently washing a microarray and which is capable of preventing a liquid sample injected into the well from being evaporated, a well plate for a microarray processing apparatus, a microarray holder, and a microarray washing method.

Means for Solving Problem

According to an aspect of the invention to accomplish the above-described object, there is provided a microarray processing apparatus that performs a hybridization process and a washing process with respect to a microarray. The microarray processing apparatus includes a well plate in which one or two or more wells are formed, each well accommodating a microarray, and a suction nozzle that suctions a liquid from the well. The well has a concave portion whose upper end is opened, which has a depth equal to or greater than a height of the microarray, and into which a front end of the suction nozzle can be inserted up to a height position of a lower end of the microarray accommodated in the well, and the suction nozzle can relatively descend in the well until the front end of the suction nozzle is located at the height position of the lower end of the microarray accommodated in the well.

In the invention configured in this manner, it is possible to suction a liquid from the well until a liquid surface in the well is lowered to a height position of the lower end of the microarray by using the suction nozzle which descends until the front end thereof is located at the height position of the lower end of the microarray accommodated in the well. Accordingly, subsequently, when a wash buffer is injected into the well, the liquid inside the well and wash buffer can be sufficiently substituted with each other, and thus it is possible to sufficiently wash the microarray.

In addition, in the invention, it is preferable that the microarray processing apparatus include an injection nozzle through which a liquid is injected into the well.

In the invention configured in this manner, it is possible to inject a liquid such as a wash buffer into the well by using the injection nozzle.

In addition, in the invention, it is preferable that the concave portion of the well have a shape into which the front end of the injection nozzle can be inserted up to a height position on a lower side of an upper end of the microarray accommodated in the well, and the injection nozzle be capable of relatively descending in the well until the front end of the injection nozzle is located at a height position on a lower side of the upper end of the microarray accommodated in the well.

In the invention configured in this manner, the injection nozzle can relatively descend in the well until the front end of the injection nozzle is located at a height position on a lower side of the upper end of the microarray accommodated in the well, and thus it is possible to reliably inject a liquid such as the wash buffer into the well from the injection nozzle.

In addition, in the invention, it is preferable that the well accommodate a flat plate-shaped microarray, which is mounted on a microarray holder, in an erected state.

In the invention configured in this manner, it is possible to suction a liquid from the well until a liquid surface in the well is lowered to the height position of the lower end of the microarray by using the suction nozzle which descends until the front end thereof is located at the height position of the lower end of the microarray accommodated in the well in a state of being mounted on the microarray holder to be erected therefrom. Accordingly, subsequently, when the wash buffer is injected into the well, the liquid inside the well and wash buffer can be sufficiently substituted with each other, and thus it is possible to sufficiently wash the flat plate-shaped microarray that is mounted on the microarray holder.

In addition, in the invention, it is preferable that the microarray processing apparatus further include an input means for receiving an input of operation conditions relating to the hybridization process and the washing process, a calculation means for calculating an end scheduled time of the hybridization process and the washing process on the basis of the operation conditions that are input through the input means, and an output means for outputting a calculation result obtained by the calculation means.

In the invention configured in this manner, the output means outputs an end scheduled time of the hybridization process and the washing process which corresponds to operation conditions input through the input means, and thus a user can grasp the end scheduled time of the hybridization process and the washing process.

In addition, in the invention, it is preferable that the suction nozzle be capable of relatively descending in the well until the front end of the suction nozzle is located at a height position spaced away from a bottom surface of the well by from 1 mm to 2 mm.

In the invention configured in this manner, it is possible to suction almost all liquid from the well by using the suction nozzle that descends until it is located at the height position spaced away from the bottom surface of the well by from 1 mm to 2 mm. Accordingly, subsequently, when a wash buffer is injected into the well, the liquid inside the well and wash buffer can be sufficiently substituted with each other, and thus it is possible to sufficiently wash the microarray.

In addition, in the invention, it is preferable that a front end surface of the suction nozzle have an inclination angle of 10° or less with respect to the bottom surface of the well.

In the invention configured in this manner, it is possible to bring the entirety of the front end surface of the suction nozzle into contact with the bottom surface of the well, and thus it is possible to suction a liquid from the well until a liquid surface in the well is lowered to the vicinity of the bottom surface of the well. Accordingly, subsequently, when a wash buffer is injected into the well, the liquid inside the well and wash buffer can be sufficiently substituted with each other, and thus it is possible to sufficiently wash the microarray.

In addition, according to another aspect of the invention, there is provided a well plate for a microarray processing apparatus that performs a hybridization process and a washing process with respect to a microarray. The well plate includes one or two or more wells that accommodate a microarray. The well has a concave portion whose upper end is opened, which has a depth equal to or greater than a height of the microarray, and into which a front end of a suction nozzle that suctions a liquid from the well can be inserted up to a height position of a lower end of the microarray accommodated in the well.

In the invention configured in this manner, it is possible to suction a liquid from the well until a liquid surface in the well is lowered to a height position of the lower end of the microarray by using the suction nozzle which descends until the front end thereof is located at the height position of the lower end of the microarray accommodated in the well. Accordingly, subsequently, when a wash buffer is injected into the well, the liquid inside the well and wash buffer can be sufficiently substituted with each other, and thus it is possible to sufficiently wash the microarray.

In addition, in the invention, it is preferable that the concave portion of the well have a shape into which the front end of the suction nozzle can be inserted up to a height position on a lower side of a lower end of the microarray accommodated in the well.

In the invention configured in this manner, it is possible to suction a liquid from the well until a liquid surface in the well is lowered to a height position on a lower side of the lower end of the microarray by using the suction nozzle which descends until the front end thereof is located at the height position on a lower side of the lower end of the microarray accommodated in the well. Accordingly, subsequently, when a wash buffer is injected into the well, the liquid inside the well and wash buffer can be sufficiently substituted with each other, and thus it is possible to sufficiently wash the microarray.

In addition, in the invention, it is preferable that the concave portion of the well have a shape into which a front end of an injection nozzle through which a liquid is injected into the well can be inserted up to a height position on a lower side of an upper end of the microarray accommodated in the well.

In the invention configured in this manner, the concave portion of the well has a shape into which the front end of the injection nozzle can be inserted up to a height position on a lower side of the upper end of the microarray accommodated in the well, and thus it is possible to reliably inject a liquid such as the wash buffer into the well from the injection nozzle.

In addition, in the invention, it is preferable that the concave portion of the well have a shape into which the front end of the injection nozzle can be inserted up to a height position on a lower side of the lower end of the microarray accommodated in the well.

In the invention configured in this manner, the concave portion of the well has a shape into which the front end of the injection nozzle can be inserted up to a height position on a lower side of the lower end of the microarray accommodated in the well, and thus it is possible inject a liquid such as a wash buffer by the injection nozzle from a height position on a lower side of the lower end of the microarray. Accordingly, it is possible to sufficiently spread the liquid such as the wash buffer in the well.

In addition, according to still another aspect of the invention, there is provided a method of washing a microarray using the microarray processing apparatus. The method includes a descending process of relatively descending the suction nozzle in the well until a front end of the suction nozzle is located at a height position of a lower end of the microarray accommodated in the well, a suction process of suctioning a liquid from the well by the suction nozzle until a liquid surface in the well is lowered to a height position of the lower end of the microarray, and an injection process of injecting a wash buffer into the well by an injection nozzle after the suction process.

In the invention configured in this manner, the liquid inside the well and the wash buffer can be sufficiently substituted with each other, and thus it is possible to sufficiently wash the microarray.

In addition, in the invention, it is preferable that the descending process, the suction process, and the injection process be repeated in a plurality of times.

In the invention configured in this manner, the liquid inside the well and the wash buffer can be sufficiently substituted with each other, and thus it is possible to sufficiently wash the microarray.

In addition, in the invention, it is preferable that the descending process and the suction process be performed after the injection process, and the method further comprise a drying process of drying the microarray accommodated in the well after the descending process and the suction process.

In the invention configured in this manner, it is possible to dry a microarray that is sufficiently washed.

In addition, in the invention, it is preferable that in the descending process and the suction process, the liquid be suctioned from the well by the suction nozzle while relatively descending the suction nozzle in the well.

In the invention configured in this manner, it is possible to shorten a time taken to suction the liquid from the well.

In addition, according to still another aspect of the invention, there is provided a microarray holder that holds a flat plate-shaped microarray. The microarray holder includes a holding frame which pinches an outer edge portion of the microarray from both sides of one main surface and the other main surface of the microarray in a state in which at least the central portion of the microarray is exposed, and which faces a side end surface of the microarray. A portion of the holding frame, which faces the one main surface of the microarray, is separated from a portion of the holding frame which faces the side end surface of the microarray, and is located on an inner side of the microarray in relation to the side end surface of the microarray.

In the invention configured in this manner, the gap between the side end surface of the microarray and the holding frame that faces the side end surface is not covered with the holding frame that faces one main surface of the microarray, and thus even when a liquid sample intrudes into a space between the side end surface of the microarray and the microarray holder in the hybridization process, the wash buffer can easily intrude into the gap. Accordingly, it is possible to reliably wash the liquid sample.

In addition, in the invention, it is preferable that the holding frame include a frame main body that continuously comes into contact with an outer edge portion of the one main surface of the microarray and a side end surface that is adjacent to the outer edge portion, and a cover member that comes into contact with an outer edge portion of the other main surface of the microarray and pinches the outer edge of the microarray in combination with the frame main body. In addition, it is preferable that the cover member comes into contact with the other main surface of the microarray at a position spaced away from the side end surface of the microarray toward an inner side of the microarray.

In the invention configured in this manner, the cover member does not cover the gap between the side end surface of the microarray and the frame main body, and thus the gap can be exposed to the outside. Accordingly, the wash buffer can easily intrude into the contact surface. Accordingly, it is possible to reliably clean the liquid sample.

In addition, in the invention, it is preferable that the frame main body and the cover member pinch the outer edge of the microarray at positions that are at least partially offset in a thickness direction of the microarray.

In the invention configured in this manner, it is possible to prevent the gap between contact surfaces of the side end surface of the microarray and the frame main body from being covered, and thus the wash buffer can easily intrude into the gap. Accordingly, it is possible to reliably wash the liquid sample that intrudes into the gap.

In addition, in the invention, it is preferable that the frame main body and the cover member pinch the outer edge of the microarray at positions that are completely offset in the thickness direction of the microarray.

In the invention configured in this manner, the cover member is disposed at a position spaced away from the side end surface of the microarray, and thus it is possible to further reliably prevent the gap between the side end surface of the microarray and the frame main body from being covered. As a result, the wash buffer can more easily intrude into the gap, and thus it is possible to more reliably wash the liquid sample that intrudes into the gap.

In addition, according to still another aspect of the invention, there is provided a microarray processing apparatus that performs a hybridization process and a washing process with respect to a microarray. The microarray processing apparatus includes a well plate in which one or two or more wells are formed, each well accommodating the microarray in an erected state and having a concave portion whose upper end is opened and which has a depth deeper than a height of the microarray, and a well cover which comes into contact with an upper surface of the well plate and hermetically seals an opening of the well.

In the invention configured in this manner, in a state in which the well cover comes into contact with the upper surface of the well plate, the lower surface of the well cover and the upper end surface of the microarray are spaced away from each other, and thus it is possible to prevent the upper end surface of the microarray from being suctioned onto the lower surface of the well cover. In addition, the upper end surface of the microarray does not protrude toward an upper side of the opening surface of the well, and thus it is possible to bring the lower surface of the well cover into close contact with the upper surface of the well plate. Accordingly, it is possible to hermetically seal the opening of the well with the lower surface of the well cover.

In addition, in the invention, it is preferable that the microarray be a flat plate-shaped microarray whose outer edge is held by a microarray holder, and the concave portion of the well have a depth that is deeper than a height of the microarray holder.

In the invention configured in this manner, in a state in which the well cover comes into contact with the upper surface of the well plate, the lower surface of the well cover and the upper end surface of the microarray holder are spaced away from each other, and thus it is possible to prevent the upper end surface of the microarray holder from being suctioned onto the lower surface of the well cover. In addition, the upper end surface of the microarray holder does not protrude toward an upper side of the opening surface of the well, and thus it is possible to bring the lower surface of the well cover into close contact with the upper surface of the well plate. Accordingly, it is possible to hermetically seal the opening of the well with the lower surface of the well cover.

In addition, in the invention, it is preferable that the microarray processing apparatus further include a well cover supporting mechanism which supports the well cover in such a manner that a lower surface of the well cover faces an upper surface of the well plate on an upper side of the well plate, and which moves the well cover in a vertical direction.

In the invention configured in this manner, when the well cover is downwardly moved by the well cover supporting mechanism, thereby bringing the lower surface of the well cover into contact with the upper surface of the well plate.

In addition, in the invention, it is preferable that the well plate have a circular plate shape, a plurality of the wells be arranged in a circumferential direction of the well plate, the well cover be a circular plate-shaped member having substantially the same external appearance as the well plate, and the well cover supporting mechanism rotate the well cover around a central axis.

In the invention configured in this manner, it is possible to move the suction nozzle and the injection nozzle, which are provided to the well cover, to an upper side of an arbitrary well by rotating the well cover with the well cover supporting mechanism, and the well cover is downwardly moved, and thus it is possible to descend the suction nozzle and the injection nozzle into an arbitrary well.

Effect of the Invention

According to the microarray processing apparatus, the well plate for the microarray processing apparatus, and the method of washing the microarray according to the invention, it is possible to sufficiently substitute the liquid in the well and the wash buffer with each other, and thus it is possible to sufficiently wash the microarray.

BRIEF DESCRIPTION OF DRAWINGS

FIG. 2 is a plan view illustrating the microarray that is held by the microarray holder according to the embodiment of the invention.

FIG. 3 is a plan view illustrating a holder main body of the microarray holder according to the embodiment of the invention.

FIG. 7 is a cross-sectional view illustrating a state in which the microarray holder illustrated in FIG. 6 according to the embodiment of the invention holds the microarray, in which

FIG. 11 is a view illustrating a well of the microarray processing apparatus according to the embodiment of the invention, in which

MODE(S) FOR CARRYING OUT THE INVENTION

Hereinafter, a microarray processing apparatus, a well plate for a microarray processing apparatus, a microarray holder, and a microarray washing method according to an embodiment of the invention will be described with reference to the attached drawings.

Figure 1:
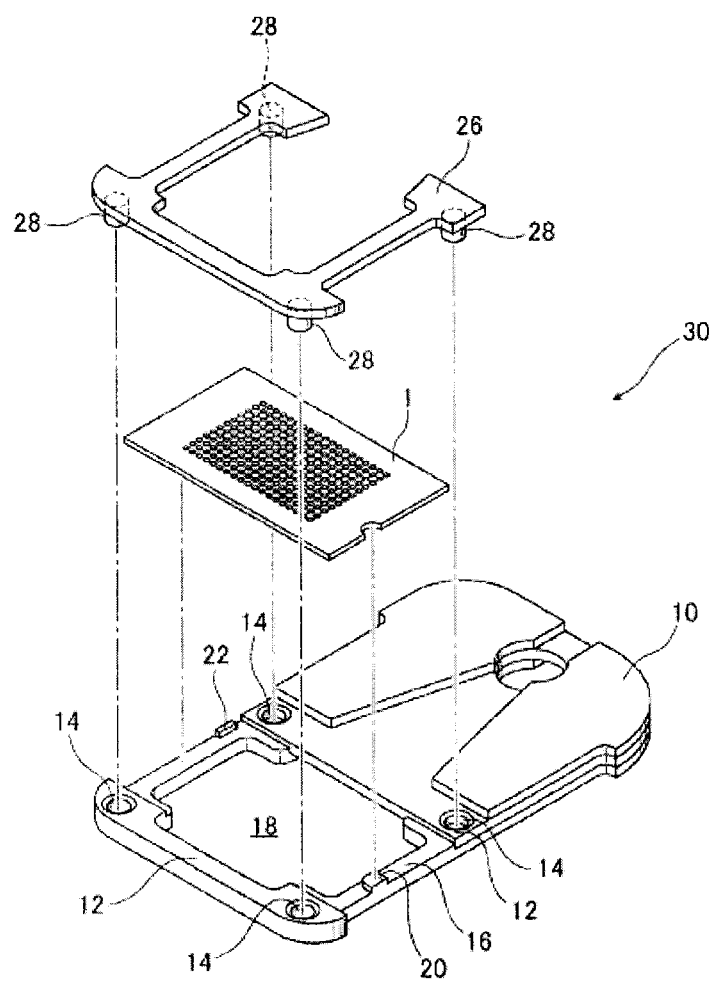
FIG. 1 is an exploded perspective view of a microarray holder and a microarray according to an embodiment of the invention.
Figure 4:
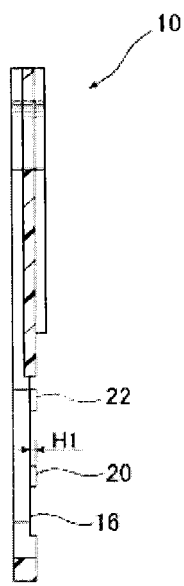
FIG. 4 is a cross-sectional view taken along a line A-A of FIG. 3.

First, the microarray and the microarray holder according to the embodiment of the invention will be described with reference to FIGS. 1 to 4. FIG. 1 is an exploded perspective view of the microarray holder and the microarray according to the embodiment of the invention, FIG. 2 is a plan view illustrating the microarray that is held by the microarray holder according to the embodiment of the invention, FIG. 3 is a plan view illustrating a holder main body of the microarray holder according to the embodiment of the invention, and FIG. 4 is a cross-sectional view taken along a line A-A of FIG. 3.

As the microarray 1 illustrated in FIGS. 1 and 2, a known microarray (Japanese Patent No. 4150330, Japanese Patent No. 3654894, and the like) may be used. For example, as illustrated in FIG. 2, in the microarray 1, a through-hole forming portion 6, which is a section having a plurality of through-holes 4 in which a polymer gel including a probe is filled, is provided at the center of a rectangular flat plate-shaped microarray main body 2. The microarray 1 has a lateral length (width) of W1, a longitudinal length (height) of L1, and a thickness of T1.

A detection object of the microarray that is used in this embodiment is not limited, and examples thereof include DNA, RNA, protein, chemical materials, and the like. A kind of the microarray is also not limited, but a through-hole type microarray is preferable. This is because an effect of the microarray holder of this embodiment is easily exhibited.

Hereinafter, an aspect of the through-hole type microarray will be described. The microarray can be manufactured by the following processes (i) to (iv).

Process (i): Process of Three-Dimensionally Arranging a Plurality of Pieces of Hollow Fiber in Such a Manner that Respective Fiber Axes of the Plural Pieces of Hollow Fiber are Arranged in the Same Direction as Each Other, and Fixing this Arrangement with a Resin to Manufacture a Hollow Fiber Bundle A method of forming a through-hole is not particularly limited, and for example, similar to a method described in Japanese Unexamined Patent Application Publication No. 2001-133453, a method of manufacturing an arranged body in which a plurality of pieces of hollow fiber are arranged in a coaxial direction, and then curing the arranged body with a resin may be used. As the hollow fiber, various materials may be used, and an organic material is preferable.

Examples of hollow fiber formed from an organic material include polyamide-based hollow fiber such as nylon 6, nylon 66, and aromatic polyamide, polyester-based hollow fiber such as polyethylene terephthalate, polybutylene terephthalate, polylactic acid, polyglycolic acid, and polycarbonate, acryl-based hollow fiber such as polyacrylonitrile, polyolefin-based hollow fiber such as polyethylene and polypropylene, polymethacrylate-based hollow fiber such as polymethyl methacrylate, polyvinyl alcohol-based hollow fiber, polyvinylidene chloride-based hollow fiber, polyvinyl chloride-based hollow fiber, polyurethane-based hollow fiber, phenol-based hollow fiber, fluorine-based hollow fiber formed from polyvinylidene fluoride or polytetrafluoroethylene, polyalkylene paraoxybenzoate-based hollow fiber, and the like. The hollow fiber may be porous, and may be obtained by a known porosity giving technology such as a stretching method by a melt spinning method or a solution spinning method, a microphase separation method, and an extraction method. The porosity is not particularly limited, but from the viewpoint of increasing a density of a probe that is fixed in the vicinity of a fibrous material unit length, high porosity is preferable to obtain a large specific surface area. An inner diameter of the hollow fiber may be set in an arbitrary manner. It is preferable that the inner diameter be set to 10 μm to 2000 μm, and more preferably 150 μm to 1000 μm.

A method of manufacturing the hollow fiber is not limited, and the hollow fiber may be manufactured by a known method such as a method described in Japanese Unexamined Patent Application Publication No. H11-108928. For example, a melt spinning method is preferable, and as a nozzle, a horseshoe-shaped or C-shaped nozzle, a double-pipe nozzle, and the like may be used. In this embodiment, it is preferable to use the double-tube nozzle when considering that a continuous uniform hollow portion can be formed.

In addition, hollow fiber which contains an appropriate amount of a black pigment such as carbon black may be used as necessary. When containing the black pigment, it is possible to reduce optical noise that is derived from impurities such as dust during detection, or it is possible to increase the strength of the resin. The amount of the pigment is not limited, and may be appropriately selected according to a size of the hollow fiber, an intended use of the microarray, and the like. For example, the amount of the pigment may be set to 0.1% by mass to 10% by mass, preferably 0.5% by mass to 5% by mass, and more preferably 1% by mass to 3% by mass.

When manufacturing a block body, a method of performing fixing with a resin such as an adhesive in order for arrangement of an arranged body not to be scattered may be used. For example, a method in which a plurality of pieces of hollow fiber are disposed in parallel with a predetermined gap on a sheet-shaped material such as an adhesive sheet to obtain sheet-shaped fiber, and this resultant sheet is wound in a spiral shape (refer to Japanese Unexamined Patent Application Publication No. H11-108928).

In addition, the following method may be exemplified. Specifically, two porous sheets having a plurality of holes formed with a predetermined gap are made to overlap with each other in a state in which hole portions match each other. Then, hollow fiber is allowed to pass through the hole portions, and then a gap between the two porous sheets is opened to fill a curable resin material into a space at the periphery of the hollow fiber between the two porous sheets (refer to Japanese Unexamined Patent Application Publication No. 2001-133453).

It is preferable that a curable resin raw material be an organic material such as a polyurethane resin and an epoxy resin. Specifically, it is preferable that the curable resin raw material formed by one or more kinds of materials composed of organic polymers and the like. Examples of the organic polymer include a rubber material such as polyurethane, a silicon resin, and an epoxy resin, a polyamide-based resin such as nylon 6, nylon 66, and aromatic polyamide, a polyester-based resin such as polyethylene terephthalate, polybutylene terephthalate, polylactic acid, polyglycolic acid, and polycarbonate, an acryl-based resin such as polyacrylonitrile, a polyolefin-based resin such as polyethylene and polypropylene, a polymethacrylate-based resin such as polymethyl methacrylate, a polyvinyl alcohol-based resin, a polyvinylidene chloride-based resin, a polyvinyl chloride-based resin, a phenol-based resin, a fluorine-based resin formed from polyvinylidene fluoride or polytetrafluoroethylene, a polyalkylene paraoxybenzoate-based resin, and the like. The organic polymer may contain an appropriate amount of black pigment such as carbon black. When the black pigment is added to the organic polymer, it is possible to reduce optical noise that is derived from impurities such as dust during detection, or it is possible to increase the strength of the resin. The amount of the pigment is not limited, and may be appropriately selected according to a size of the hollow fiber, an intended use of the microarray, and the like. For example, the amount of the pigment may be set to 0.1% by mass to 10% by mass, preferably 0.5% by mass to 5% by mass, and more preferably 1% by mass to 3% by mass.

The number of the hollow fiber that is arranged in this embodiment, that is, the number of spots is not limited, and may be appropriately selected according to an intended test and the like. Accordingly, a distance between plural pieces of hollow fiber may be appropriately selected according to an area of the microarray, the number of hollow fiber that is arranged, and the like.

Process (ii): Process of Introducing a Gel-Precursor Solution Containing Four Groups of Genes Selected as Described Above or a Part of the Genes into a Hollow Portion of Each Hollow Fiber of a Hollow Fiber Bundle A kind of a gel material that is filled in hollow yarn is not particularly limited, and in addition to polysaccharide such as agarose and sodium alginate, protein such as gelatin and polylysine may be used as long as the gel material is obtained from a natural material. As a synthetic polymer, a gel, which is obtained by allowing a polymer having a reactive functional group such as polyacroyl succinimide and a crosslinking agent exhibiting reactivity to react with each other, may be used. In addition to this, a synthetic polymer gel, which is obtained by copolymerization between a polymeric monomer such as acrylamide, N,N-dimethyl acrylamide, N-isopropyl acrylamide, N-acryloyl amino ethoxy ethanol, N-acryloyl amino propanol, N-methylol acrylamide, N-vinylpyrrolidone, hydroxyethyl methacrylate, (meth)acrylic acid, and allyl dextrin as a monomer and a multifunctional monomer such as methylene bis(meth)acrylamide, and polyethylene glycol di(meth)acrylate, is preferable.

A concentration of the gel that is used in the microarray of this embodiment is not particularly limited, and may be appropriately selected according to a length of the probe that is used and an amount thereof. For example, it is preferable that the concentration of the gel be 2% by mass to 10% by mass in terms of a concentration of a monomer component, more preferably 3% by mass to 7% by mass, and still more preferably 3.5% by mass to 5% by mass. The reason of limiting the concentration to 2% by mass or more is that the probe can be reliably fixed, and thus detection of a target material can be efficiently performed. In addition, the reason of limiting the concentration to 10% by mass or less is that even when the concentration is set to be more than 10% by mass, a dramatic effect is hardly obtained.

In a case of retaining the synthetic polymer gel in the microarray of the through-hole substrate, the synthetic polymer gel may be retained by filling a gel precursor solution of the synthetic polymer in the block and gelating the gel precursor solution in the block. With regard to a method of filling the gel precursor solution in the through-hole of the block, for example, the solution is suctioned into a syringe having a minute needle, and the needle is stuck into the hollow portion of each hollow fiber, thereby introducing the gel precursor solution into the hollow portion. In addition, the hollow portion of the hollow fiber bundle at a fixed end is sealed, and the other hollow portion at an end portion that is not fixed is maintained in an open state. Next, a gel precursor solution containing a nucleic acid probe having a polymerization reaction site such as a methacryl group at a distal end is prepared, and the gel precursor solution and the hollow fiber bundle are placed in a desiccator. Then, the end portion of the hollow fiber bundle at which the hollow fiber is not fixed is immersed in the solution. Then, the desiccator is decompressed and is returned to a normal pressure, thereby introducing the solution into the hollow portion of the hollow fiber from the end portion of the hollow fiber which is immersed in the solution.

Process (iii): Process of Allowing Reaction of the Gel Precursor Solution Introduced into the Hollow Portion of the Hollow Fiber Bundle to Occur, and Retaining a Gel-Like Material Containing the Probe in the Hollow Portion of the Hollow Fiber The gel-like material containing the probe is retained in the hollow portion of the hollow fiber by polymerizing the gel precursor solution that is introduced into the hollow portion of the hollow fiber. Polymerization conditions are not particularly limited, and may be appropriately selected according to a kind of the gel precursor that is used. For example, in a case of the acrylamide-based monomer, the polymerization may be performed by using a radical initiator, and preferably, the polymerization may be performed by thermal polymerization reaction using an azo-based initiator.

A kind of the probe or a size thereof is not limited, and may be appropriately selected according to a kind of a material or a compound that becomes a detection target.

Process (iv): Process of Cutting the Hollow Fiber Bundle in a Direction Intersecting a Longitudinal Direction of the Fiber and Thinning the Same The cutting method is not particularly limited as long as a thin piece is obtained. For example, the cutting may be performed by a microtome, laser, and the like. The thickness of a thin piece that is obtained is not limited, and may be appropriately selected according to the purpose of experiment. For example, the thickness may be set to 5 mm or less, and preferably 0.1 mm to 1 mm.

As illustrated in FIG. 2, a semi-circular cut-out portion 8 is provided on one side (a right short side in FIG. 1) of a microarray main body 2. When mounting the microarray 1 on the microarray holder, the cut-out portion 8 serves as a guide to allow the microarray 1 to be mounted in a correct mounting direction with respect to the microarray holder.

As illustrated in FIGS. 1, 3, and 4, a holder main body 10 is an approximately rectangular plate-shaped member and has a lateral length (width) of W2 and a longitudinal length (height) of L2. One side region (lower side), which is divided in a longitudinal direction at an approximately center of the holder main body 10, is formed as a cover member mounting portion 12 on which a cover member 26 is mounted. The cover member mounting portion 12 has a lateral length (width) of W2 and a longitudinal length (height) of L3. In addition, the cover member mounting portion 12 is formed in a thickness that is smaller than the thickness of other regions of the holder main body 10 by a thickness of the cover member 26. Accordingly, when the cover member 26 is mounted on the cover member mounting portion 12, a surface of the cover member 26 and a surface of the holder main body 10 are approximately flush with each other. Four pin holes 14 that can accommodate four pins 28 formed in the cover member 26 are formed at four corners of the cover member mounting portion 12.

In addition, a groove 16 is formed to penetrate the holder main body 10 in a lateral direction at an approximately center of the cover member mounting portion 12. The width (longitudinal length) L4 of the groove 16 is approximately the same as the longitudinal length L1 of the microarray 1. The thickness of the holder main body 10 at the groove 16 is smaller than the thickness of the cover member mounting portion 12 by the thickness T1 of the microarray 1. Accordingly, when the microarray is mounted in the groove 16, the surface of the microarray 1 and the surface of the cover member mounting portion 12 are approximately flush with each other.

A rectangular opening 18 is formed at the center of the groove 16. The opening 18 is formed in a size capable of exposing the through-hole forming portion 6 to the outside when the microarray holder holds the microarray 1.

In addition, a protrusion 20, which comes into contact with the cut-out portion 8 of the microarray 1 when the microarray 1 is held by the microarray holder, is formed in the groove 16. The protrusion 20 has a semi-circular shape that corresponds to the cut-out portion 8 of the microarray 1.

In addition, a guide 22, which comes into contact with a side end surface 2a of the microarray 1, is formed at a side approximately opposite to the protrusion 20 with the opening 18 interposed therebetween. The guide 22 is formed in a rectangular shape. The height H1 of the protrusion 20 and the guide 22 that protrude from the groove 16 is approximately the same as the thickness T1 of the microarray 1. In addition, a lateral distance W3 between the protrusion 20 and the guide 22 is approximately the same as the lateral length W1 of the microarray 1.

When the microarray 1 is accommodated in the groove 16 formed as described above, an outer edge of one main surface of the microarray 1 comes into contact with the bottom surface of the groove 16. In addition, the cut-out portion 8 of the microarray 1 comes into contact with the protrusion 20 of the holder main body 10, and in short sides of the microarray 1, a side end surface 2a of short sides not having the cut-out portion 8 comes into contact with the guide 22 of the holder main body 10. That is, the holder main body 10 continuously comes into contact with the outer edge of the one main surface of the microarray 1 and the side end surface 2a that is adjacent to the outer edge at a portion in which the protrusion 20 and the guide 22 are provided. In addition, side end surfaces 2a of both long sides of the microarray 1 come into contact with step portions between the groove 16 and other portions of the holder main body 10. According to this, movement of the microarray 1 along the bottom surface of the groove 16 is regulated.

In addition, a concave portion 24 having a predetermined depth is formed at the side end surfaces of the both long sides of the holder main body 10 along an accommodation direction (in FIG. 3, the longitudinal direction of the holder main body 10) when the holder main body 10 is accommodated in a well of a known microarray processing apparatus. Since the concave portion 24 is formed, during a process of washing the microarray 1, a wash buffer can widely spreads between the both main surfaces of the microarray 1 held by the microarray holder through the concave portion 24. Accordingly, it is possible to wash the microarray 1 in a more efficient manner.

Figure 5:
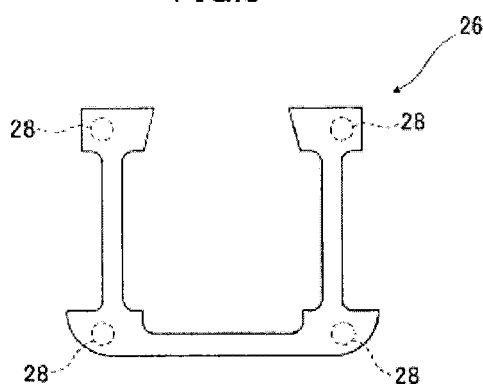
FIG. 5 is a plan view illustrating a cover member of the microarray holder according to the embodiment of the invention.

FIG. 5 is a plan view illustrating the cover member 26 of the microarray holder according to this embodiment of the invention.

As illustrated in FIGS. 1 and 5, the cover member 26 is a plate-shaped member having a U-shape. Four circular column-shaped pins 28 are formed on one surface of the cover member 26, and when the pins 28 are interested into the corresponding pin holes 14 of the cover member mounting portion 12, the cover member 26 is mounted on the cover member mounting portion 12 in a state of matching to the outer edge of the opening 18 of the holder main body 10. According to this, the cover member 26 comes into contact with an outer edge of one main surface of the microarray 1 (main surface not coming into contact with the holder main body 10), and pinches the outer edge of the microarray 1 in combination with the holder main body 10.

On the other hand, the material of the holder main body 10 and the cover member 26 is an arbitrary material not containing a material which blocks a hybridization reaction, an antigen-antibody reaction, and the like. For example, as the material, a thermoplastic material such as polypropylene, polyethylene, polymethyl methacrylate, and polycarbonate may be used. According to this material, it is possible to manufacture the microarray holder with injection molding at low cost.

In a case of performing detection using fluorescence, when intrinsic fluorescence of the microarray holder is large, an S/N ratio of the detection decreases, and thus it is difficult to perform detection with high accuracy. Accordingly, when using the microarray holder for this usage, it is necessary to select a raw material with small intrinsic fluorescence. In a case of using a material with large intrinsic fluorescence, an additive that adsorbs the intrinsic fluorescence, for example, carbon black may be added.

Figure 6:
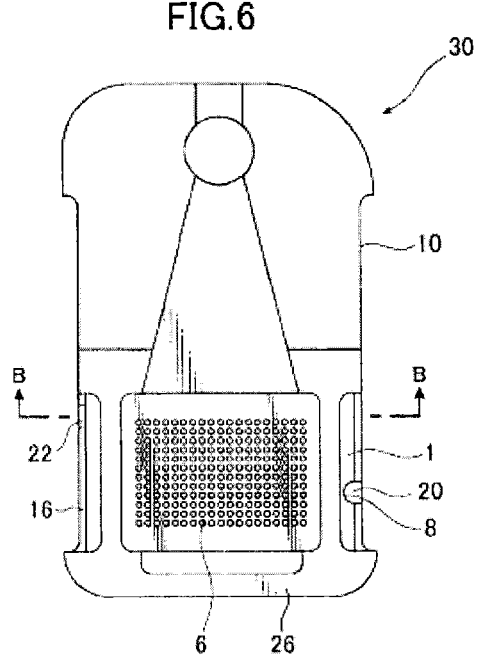
FIG. 6 is an assembly view illustrating a state in which the microarray holder according to the embodiment of the invention holds the microarray.

FIG. 6 is an assembly view illustrating a state in which the microarray holder according to the embodiment of the invention holds the microarray 1.

First, a mounting direction of the microarray 1 is determined in order for the cut-out portion 8 of the microarray 1 to come into contact with the protrusion 20 of the holder main body 10, and then the microarray 1 is provided in the groove 16. Subsequently, the cover member 26 is mounted on the cover member mounting portion 12 in such a manner that the respective pins 28 of the cover member 26 are inserted into the corresponding pin holes 14 of the cover member mounting portion 12. According to this, an outer region of the through-hole forming portion 6 of the microarray 1, that is, the outer edge of the microarray 1 is pinched by the periphery of the opening 18 in the groove 16 of the holder main body 10 and the cover member 26. That is, the periphery of the opening 18 in the groove 16 of the holder main body 10 and the cover member 26 pinch the outer edge of the microarray 1 from both sides of one main surface and the other main surface of the microarray 1 in a state in which at least the central portion of the microarray 1 is exposed to the outside, and become a holding frame that faces a side end surface 2a of the microarray 1.

Figure 7A:
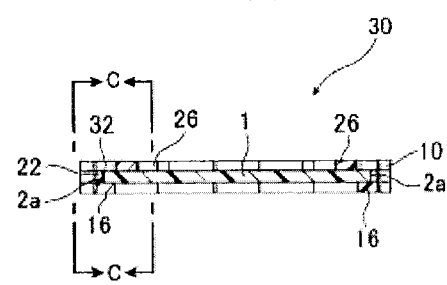
FIG. 7(a) is a cross-sectional view along a line B-B illustrated in FIG. 6.
Figure 7B:
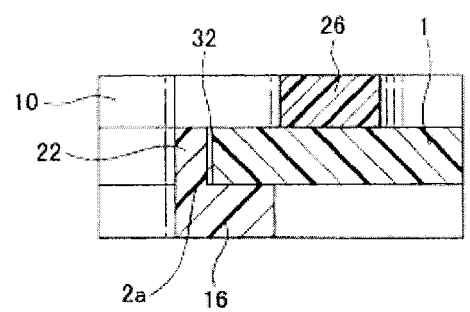
FIG. 7(b) is a partially enlarged cross-sectional view of a portion indicated by a line C-C in FIG. 7(a).

FIG. 7 is a cross-sectional view illustrating a state in which the microarray holder 30 according to the embodiment of the invention holds the microarray 1, in which FIG. 7(*a*) is a cross-sectional view taken along a line B-B illustrated in FIG. 4, and FIG. 7(b) is a partially enlarged cross-sectional view of a portion indicated by a line C-C in FIG. 7(a).

As illustrated in FIG. 7, at a position of the guide 22, the bottom surface of the groove 16 of the holder main body 10 and the side surface of the guide 22 continuously come into contact with an outer edge of one main surface (lower surface in FIG. 7) of the microarray 1 and a side end surface 2a that is adjacent to the outer edge. The cover member 26 that faces the other main surface (upper surface in FIG. 7) of the microarray 1 is separated from the guide 22 of the holder main body 10 that faces the side end surface 2a of the microarray 1, and is positioned on an inner side of the microarray 1 from the side end surface 2a of the microarray 1.

More specifically, the cover member 26 comes into contact with the other main surface (upper surface in FIG. 7) of the microarray 1 at a position that is spaced away from the side end surface 2a of the microarray 1 toward an inner side of the microarray 1. That is, the cover member 26 does not cover a gap 32 between the side end surface 2a of the microarray 1 and the guide 22 of the holder main body 10, and thus the gap 32 is opened to the outside (upper side in FIG. 7).

In this manner, the gap 32 between the holder main body 10 and the side end surface 2a of the microarray 1 is not covered with the cover member 26 at a position of the guide 22 at which the holder main body 10 continuously comes into contact with the outer edge of the one main surface of the microarray 1 and the side end surface 2a that is adjacent to the outer edge, and thus even when a liquid sample enters the gap 32 between the holder main body 10 and the side end surface 2a of the microarray 1 at a position of the guide 22 during the hybridization process, a wash buffer can easily intrude into the gap 32. Accordingly, it is possible to reliably wash the liquid sample with the wash buffer. This is true of a position of the protrusion 20 at which the holder main body 10 continuously comes into contact with the outer edge of the one surface of the microarray 1 and the side end surface 2a that is adjacent to the outer edge.

Particularly, it is preferable that the groove 16 of the holder main body 10 and the cover member 26 pinch the outer edge of the microarray 1 at positions that are at least partially offset in a thickness direction of the microarray 1, and more preferably at positions that are completely offset. That is, as illustrated in FIG. 7(b) in an enlarged manner, a region in which the groove 16 of the holder main body 10 comes into contact with one main surface (lower surface in FIG. 7) of the microarray 1, and a region in which the cover member 26 comes into contact with the other main surface (upper surface in FIG. 7) of the microarray 1 are set not to overlap with each other at all in the thickness direction of the microarray 1. When the holder main body 10 and the cover member 26 are formed in this manner, the cover member 26 is disposed at a position that is sufficiently spaced away from the side end surface 2a of the microarray 1, and thus it is possible to more reliably prevent the gap 32 between the holder main body 10 and the side end surface 2a of the microarray 1 from being covered. As a result, the wash buffer can more easily intrude into a space between the holder main body 10 and the side end surface 2a of the microarray 1, and thus it is possible to reliably wash the liquid sample with the wash buffer.

Figure 8:
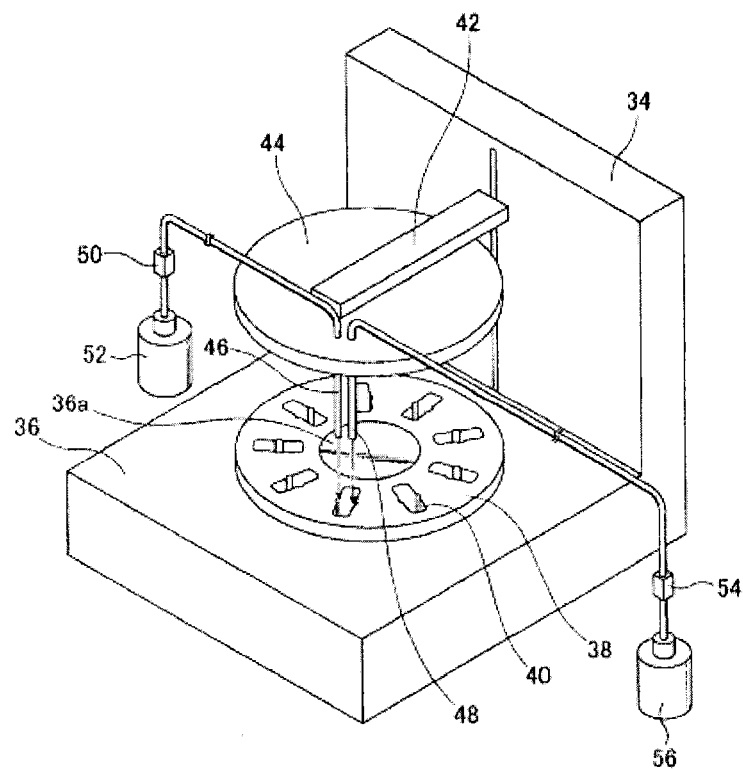
FIG. 8 is a perspective view illustrating a microarray processing apparatus according to the embodiment of the invention.

Next, a configuration of the microarray processing apparatus according to the embodiment of the invention will be described with reference to FIG. 8. FIG. 8 is a perspective view illustrating the microarray processing apparatus according to the embodiment of the invention.

As illustrated in FIG. 8, a base 36 is provided to the microarray processing apparatus 34. A circular plate-shaped well plate 38 is detachably mounted on an upper surface of the base 36. A plurality of wells 40 that accommodate the microarray 1 are arranged on an upper surface of the well plate 38 in a circumferential direction of the well plate 38. Each of the wells 40 is formed in an elongated bottomed-hole shape having an upward opening. On the other hand, the base 36 is provided with a known temperature controller (not illustrated) that uses a Peltier element, a heater, and the like, and temperature control of the well plate 38 is performed by the temperature controller. In addition, the base 36 is provided with a known liquid leakage sensor of an optical type, an electric wave type, and the like, and when a liquid overflows from the well 40, the leakage can be detected.

In addition, the microarray processing apparatus 34 includes a well cover supporting mechanism 42. The well cover supporting mechanism 42 supports the well cover 44 on an upper side of the base 36. The well cover 44 is formed in a circular plate shape having approximately the same outer diameter as the well plate 38. The well cover supporting mechanism 42 supports the well cover 44 in such a manner that the central axis of the well cover 44 and the central axis of the well plate 38 become substantially the same as each other, and a lower surface of the well cover 44 and an upper surface of the well plate 38 face each other. In addition, the well cover supporting mechanism 42 includes a linear motion mechanism that linearly moves the well cover 44 in a vertical direction along the central axial line of the well cover 44, and a rotation mechanism that rotates the well cover 44 around the central axis thereof (all of the mechanisms are not illustrated). When the well cover 44 is downwardly moved by the linear motion mechanism, the lower surface of the well cover 44 comes into contact with the well plate 38.

A suction nozzle 46 that suctions a liquid from the well 40 and an injection nozzle 48 that injects the liquid into the well 40 are provided on a lower surface of the well cover 44. When the well cover 44 is rotated by the rotation mechanism, the suction nozzle 46 and the injection nozzle 48 are moved to an upper side of any one of the wells 40. In addition, when the well cover 44 is downwardly moved by the linear motion mechanism, the suction nozzle 46 and the injection nozzle 48 descend into the well 40.

The suction nozzle 46 is formed in a length with which the front end thereof can descend until the front end is located at a height position on a lower side of the lower end of the microarray 1 accommodated in the well 40. That is, the suction nozzle 46 is longer than a length from an opening of the well 40 to the lower end of the microarray 1, and is shorter than a length from the opening of the well 40 to the bottom surface thereof (depth of the well 40).

Figure 9:
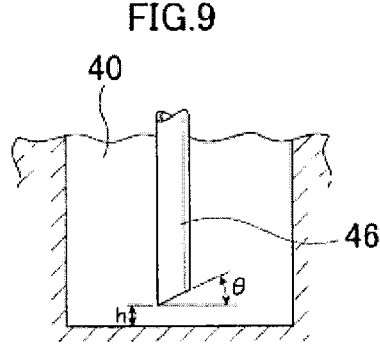
FIG. 9 is a partially enlarged side view illustrating a front end of a suction nozzle and a bottom surface of a well according to the embodiment of the invention.

FIG. 9 is a partially enlarged side view illustrating the front end of the suction nozzle 46 and the bottom surface of the well 40. As illustrated in FIG. 9, the suction nozzle 46 is preferably formed in a length with which the suction nozzle 46 can descend in the well 40 until the height h of the front end of the suction nozzle 46 from the bottom surface of the well 40 becomes from 1 mm to 2 mm. In addition, the suction nozzle 46 is preferably formed in such a manner that an inclination angle $\theta$ of a front end surface of the suction nozzle 46 with respect to the bottom surface of the well 40 (angle made by the bottom surface of the well 40 and the front end surface of the suction nozzle 46) becomes 10° or less. Particularly, the suction nozzle 46 is preferably formed in such a manner that the front end surface of the suction nozzle 46 becomes parallel with the bottom surface of the well 40 (inclination angle $\theta$ becomes) 0°.

In addition, the suction nozzle 46 is connected to a waste liquid recovery bottle 52 through a suction pump 50. The suction pump 50 that is connected between the suction nozzle 46 and the waste liquid recovery bottle 52 conveys a liquid from the suction nozzle 46 to the waste liquid recovery bottle 52. According to this, the liquid that is suctioned from the well 40 by the suction nozzle 46 is recovered in the waste liquid recovery bottle 52. The suction pump 50 is a pump capable of conveying a gas-liquid mixed fluid, and for example, a diaphragm pump may be used. A known liquid surface meter of a floating type, an optical type, an electrostatic capacitance type, and the like is provided to the waste liquid recovery bottle 52. A detection value obtained by the liquid surface meter is output to a controller (not illustrated).

For example, the injection nozzle 48 is formed in approximately the same length as the suction nozzle 46.

In addition, the injection nozzle 48 is connected to a wash buffer bottle 56 through an injection pump 54. The injection pump 54 that is connected between the injection nozzle 48 and the wash buffer bottle 56 suctions the wash buffer from the wash buffer bottle 56 and ejects a predetermined amount of wash buffer to the injection nozzle 48. The injection pump 54 is a pump capable of ejecting a predetermined amount of fluid, and for example, a syringe pump may be used. On the other hand, the injection pump 54 may be connected to a plurality of the wash buffer bottles 56 through a valve. The wash buffer bottle 56 that suctions the wash buffer can be selected by changing the valve, and a different kind of wash buffer can be injected into the well 40 from the injection nozzle 48. A known liquid surface meter of a floating type, an optical type, an electrostatic capacitance type, and the like is provided to the wash buffer bottle 56. A detection value obtained by the liquid surface meter is output to a controller (not illustrated).

Figure 10:
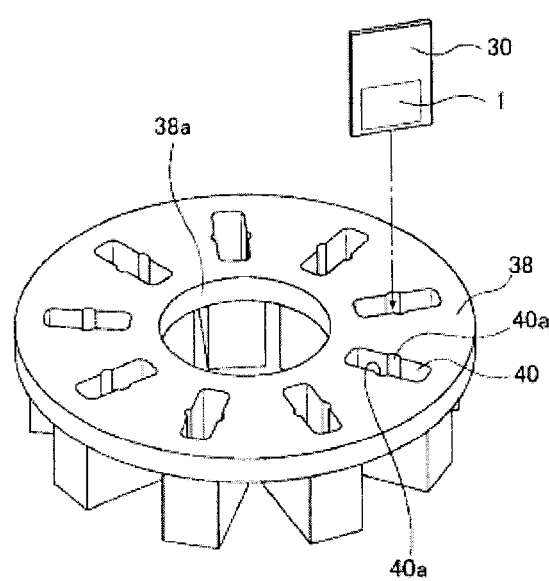
FIG. 10 is a perspective view illustrating a well plate for the microarray processing apparatus according to the embodiment of the invention.

Next, a configuration of the well plate 38 of the microarray processing apparatus 34 according to the embodiment of the invention will be described with reference to FIG. 10. FIG. 10 is a perspective view illustrating the well plate 38 of the microarray processing apparatus 34 according to the embodiment of the invention.

As illustrated in FIG. 10, the well plate 38 is formed in a circular plate shape. When a circular hole 38a that is formed at the center of the well plate 38 is inserted around a circular column-shaped protrusion 36a that is formed on an upper surface of the base 36, the well plate 38 is mounted on the base 36.

A plurality of wells 40, which accommodate the microarray 1 in an erected state, are arranged in the well plate 38 along a circumferential direction of the well plate 38. As illustrated in FIG. 10, the well 40 is formed in an elongated bottomed-hole shape having an upward opening. The microarray holder 30 that holds the microarray 1 is accommodated in each of the wells 40.

Figure 11A:
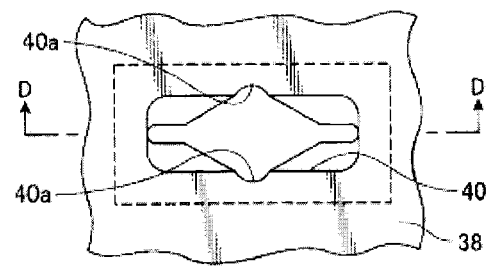
FIG. 11(a) is a top view of a well.
Figure 11B:
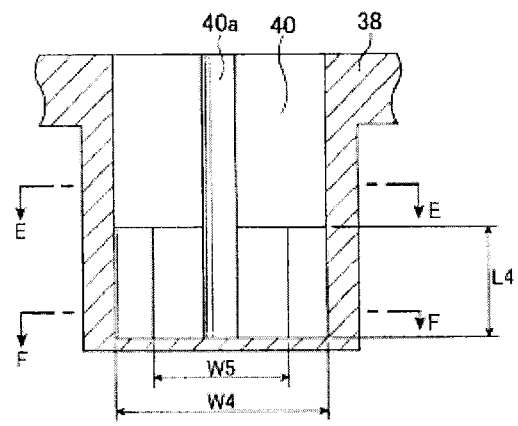
FIG. 11(b) is a cross-sectional view of the well illustrated in FIG. 11(a) which is taken along a line D-D.
Figure 11C:
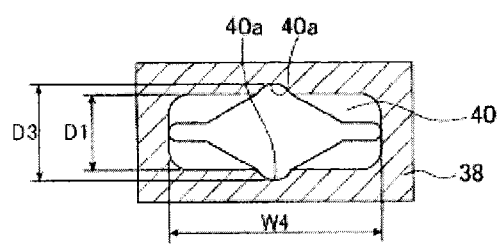
FIG. 11(c) is a cross-sectional view of the well illustrated in FIG. 11(b) which is taken along a line E-E.
Figure 11D:
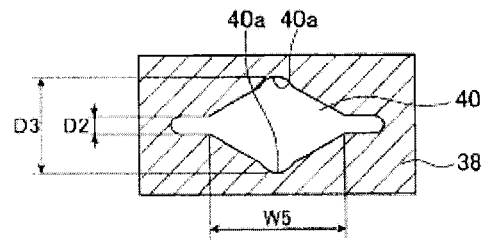
FIG. 11(d) is a cross-sectional view of the well illustrated in FIG. 11(b) which is taken along a line F-F.

Next, a structure of the well 40 of the microarray processing apparatus 34 according to the embodiment of the invention will be described in detail with reference to FIGS. 11 and 12. FIG. 11 is a view illustrating the well 40 of the microarray processing apparatus 34 according to the embodiment of the invention, in which FIG. 11(a) is a top view, FIG. 11(b) is a cross-sectional view of the well 40 illustrated in FIG. 11(a) which is taken along a line D-D, FIG. 11(c) is a cross-sectional view of the well 40 illustrated in FIG. 11(b) which is taken along a line E-E, and FIG. 11(d) is a cross-sectional view of the well 40 illustrated in FIG. 11(b) which is taken along a line F-F. In addition, FIG. 12 is a cross-sectional view of the well 40 in which the microarray 1 held by the microarray holder 30 is accommodated.

Figure 12:
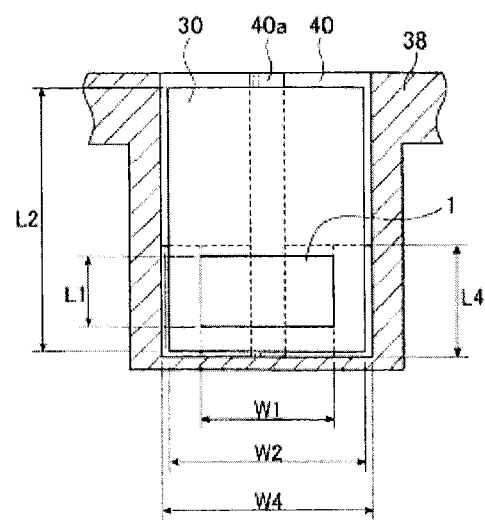
FIG. 12 is a cross-sectional view of the well in which the microarray held by the microarray holder is accommodated.

As illustrated in FIGS. 11 and 12, the well 40 is formed to have a concave shape whose upper end is opened and which has a depth deeper than the height of the microarray 1. In the following description, among respective dimensions of the well 40, a length along a longitudinal direction of the opening of the well 40 (a left-right direction in FIG. 11) is called a width of the well 40, and a length along a direction perpendicular to the longitudinal direction of the opening of the well 40 (that is, the thickness direction of the microarray holder 30 accommodated in the well. A vertical direction in FIGS. 11(a), 11(c), and 11(d)) is called an inner length of the well 40.

On the other hand, as is the case with the description with reference to FIGS. 2 and 3, among respective dimensions of the microarray holder 30 and the microarray 1, a length (height) of the microarray 1 along an accommodation direction of the microarray holder 30 into the well 40 is L1, a length (height) of the microarray holder 30 is L2, a length (width) of the microarray 1 along the longitudinal direction of the opening of the well 40 is W1, and a length (width) of the microarray holder 30 is W2. In addition, the plate thickness of the microarray holder 30 is set to T2.

The width of the well 40 is set to a predetermined width W3 that is larger than the width W2 of the microarray holder 30 in a range from the bottom surface of the well 40 to the opening thereof. In addition, the inner length D1 of the well 40 is set in such a manner that in a range from a position on an upper side of the bottom surface of the well 40 by a length L4 to the opening of the well 40, a gap (D1−T2)/2 between an inner wall of the well 40 and the microarray holder 30 is equal to or greater than a length G. Here, the length G is, for example, a length with which a front end of a pair of tweezers can be inserted between the inner wall of the well 40 and the microarray holder 30 to grip the microarray holder 30 accommodated in the well 40. In addition, for example, the length L4 is a length from the bottom surface of the well 40 to the upper end of the microarray 1 that is held by the microarray holder 30 accommodated in the well 40.

That is, the well 40 is formed as described below. On an upper side of the height position of the upper end of the accommodated microarray 1, a gap between the inner wall of the well 40 and the microarray 1 is formed to be equal to or longer than the length G. In addition, as illustrated in FIG. 12, the upper end of the microarray holder 30 is located on an upper side of the upper end of the microarray 1 that is mounted on the microarray holder 30. Accordingly, on an upper side of the height position of the upper end of the microarray 1, the pair of tweezers can be inserted between the inner wall of the well 40 and the microarray holder 30 to easily grip the microarray holder 30.

On the other hand, it is not necessary to inject the liquid sample on an upper side of the height position of the upper end of the microarray 1 that is held by the microarray holder 30 accommodated in the well 40. Accordingly, the gap between the inner wall of the well 40 and the microarray holder 30 is set to be equal to or larger than the length G. As a result, even when a volume of the well 40 increases, an amount of the liquid sample to be injected into the well 40 does not increase, and thus a problem does not occur.

On the other hand, in a range from the bottom surface of the well 40 to a position on an upper side of the bottom surface by a length L4, the inner length D2 of the well 40 is slightly larger than the plate thickness T2 of the microarray holder 30. According to this, the microarray holder 30 is pinched by the inner wall of the well 40, and a volume of a range in which the liquid sample is injected into the well 40 (that is, a range from the bottom surface of the well 40 to a position on an upper side of the bottom surface by the length L4) can be as small as possible. In this case, the gap (D2−T2)/2 between the inner wall of the well 40 and the microarray holder 30 is made to be smaller than an outer diameter N1 of the suction nozzle 46 and an outer diameter N2 of the injection nozzle 48. Accordingly, in a range from the bottom surface of the well 40 to a position on an upper side of the bottom surface by the length L4 (that is, a height position on a lower side of the upper end of the microarray 1 that is accommodated), the suction nozzle 46 and the injection nozzle 48 cannot be inserted between the inner wall of the well 40 and the microarray holder 30. On the other hand, in this embodiment, the inner length D2 of the well 40 is smaller than D1.

In addition, a concave portion 40*a* having a dimensional shape into which the suction nozzle 46 and the injection nozzle 48 can be inserted is formed at the inner wall of the well 40 from the bottom surface of the well 40 to the opening. Specifically, a concave portion 40*a*, which extends along an accommodation direction (a vertical direction in FIG. 11(*b*)) of the microarray holder 30 and has an arc-shaped cross-section, is formed at an approximately center of each inner wall that faces each of both surfaces of the microarray holder 30 accommodated in the well 40. A diameter of an arc-shaped cross-section of the concave portion 40*a* is larger than the outer diameter N1 of the suction nozzle 46 and the outer diameter N2 of the injection nozzle 48. In addition, a length D3 between concave portions 40*a* that face each other in the well 40 is set in such a manner that a gap (D3−T2)/2 between the concave portion 40*a* and the microarray holder 30 becomes larger than the outer diameter N1 of the suction nozzle 46 and the outer diameter N2 of the injection nozzle 48. According to this, the suction nozzle 46 and the injection nozzle 48 can descend to the bottom surface of the well 40 (that is, a height position on a lower side of the lower end of the microarray 1) in the concave portion 40*a*.

In addition, in a range from the bottom surface of the well 40 to a position on an upper side of the bottom surface by a length L4, as illustrated in FIG. 11(*d*), the concave portion 40*a* is formed to have an approximately V-shaped cross-section. In the V-shaped cross-section, the above-described arc-shaped cross-section is included. A width W5 of the concave portion 40*a* having the V-shaped cross-section is approximately the same as the width W1 of the microarray 1. According to this, a triangular column-shaped space, which is surrounded by the microarray 1 that is exposed through the opening of the microarray holder 30 and the concave portion 40*a* having the V-shaped cross-section, is formed. When the wash buffer is injected into the well 40 from the injection nozzle 48, the wash buffer sufficiently spreads in the triangular column-shaped space, and thus it is possible to sufficiently wash the microarray 1.

Figure 13A:
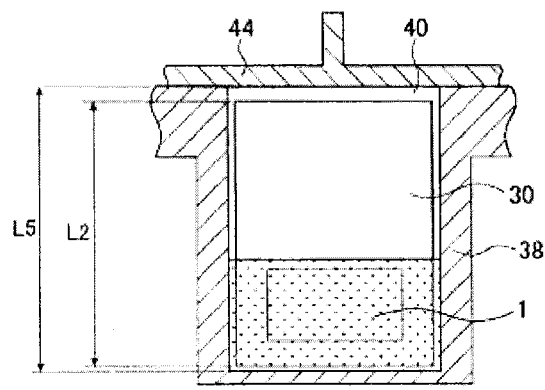
FIG. 13 is a schematic cross-sectional view of the well in which the microarray held by the microarray holder is accommodated, and a well cover.
Figure 13B:
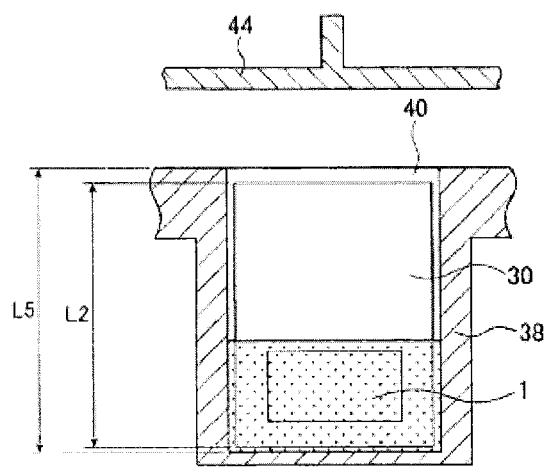

Next, a relation between the well plate 38 and the well cover 44 will be described with reference to FIG. 13. FIG. 13 is a schematic longitudinal cross-sectional view of the well 40 in which the microarray 1 held by the microarray holder 30 is accommodated and the well cover 44, in which FIG. 11(*a*) illustrates a state in which the lower surface of the well cover 44 comes into contact with the upper surface of the well plate 38, and FIG. 11(*b*) illustrates a state in which the lower surface of the well cover 44 and the upper surface of the well plate 38 are spaced away from each other.

As illustrated in FIG. 13, a depth L5 of the well 40 (length from the bottom surface that comes into contact with the lower end surface of the microarray holder 30 to the opening surface on the upper end) is larger than the height L2 of the microarray holder 30 (length from the lower end of the microarray holder 30 to the upper end thereof). Accordingly, in a state in which the microarray holder 30 is accommodated in the well 40 in such a manner that the lower end of the microarray holder 30 comes into contact with the bottom of the well 40, the upper end of the microarray holder 30 is located at a position on a lower side of the opening surface of the well 40 (for example, at a position on a lower side of the opening surface of the well 40 by 1 mm). That is, as illustrated in FIG. 13(*a*), in a state in which the lower surface of the well cover 44 comes into contact with the upper surface of the well plate 38, the lower surface of the well cover 44 and the upper end surface of the microarray holder 30 are spaced away from each other.

As a result, when the microarray holder 30 is accommodated in the well, the upper end surface of the microarray holder 30 does not upwardly protrude from the opening surface of the well 40. In addition, when the well cover 44 is downwardly moved by the linear motion mechanism of the well cover supporting mechanism 42 in a hybridization process, the lower surface of the well cover 44 can come into close contact with the upper surface of the well plate 38, and thus the opening of the well 40 may be hermetically sealed by the lower surface of the well cover 44.

In addition, even when the lower surface of the well cover 44 is brought into close contact with the upper surface of the well plate 38, the upper end surface of the microarray holder 30 is not suctioned onto the lower surface of the well cover 44. Accordingly, when the well cover 44 is upwardly moved by the linear motion mechanism of the well cover supporting mechanism 42 after performing the hybridization with respect to the microarray 1, as illustrated in FIG. 13(*b*), the microarray holder 30 is not drawn up together with the well cover 44 and can be maintained in a state of being accommodated in the well 40.

Next, a method of washing the microarray 1 by using the above-described microarray processing apparatus 34 according to the embodiment of the invention will be described with reference to FIG. 14.

Figure 14A:
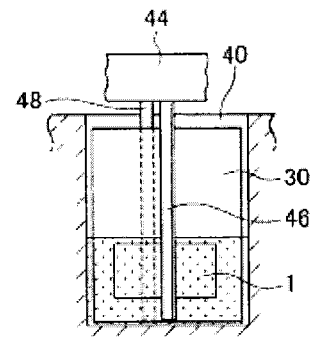
FIG. 14 is a side view schematically illustrating a microarray washing method by using the microarray processing apparatus according to the embodiment of the invention.
Figure 14B:
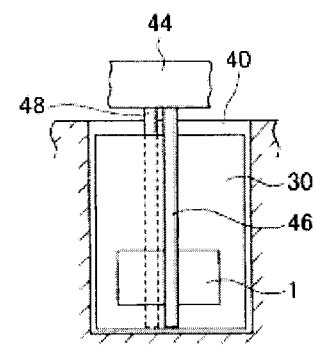
Figure 14C:
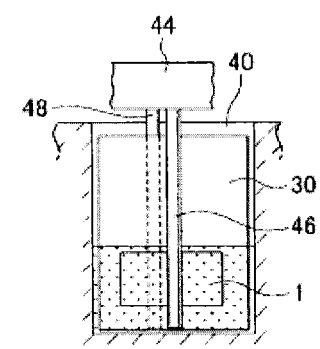

FIG. 14 is a side view schematically illustrating the method of washing the microarray 1 by using the microarray processing apparatus 34 according to the embodiment of the invention.

Prior to the washing of the microarray 1, the hybridization process with respect to the microarray 1 is performed. In the hybridization process, first, the well plate 38 is mounted on the base 36, and the microarray holder 30 that holds the microarray 1 is accommodated in each of the wells 40 of the well plate 38. In addition, the liquid sample is injected into the well 40. At this time, it is preferable that a liquid surface of the liquid sample reach the upper end of the microarray 1.

Subsequently, the controller compares an output value from the liquid surface meters of the waste liquid recovery bottle 52 and the wash buffer bottle 56, and a reference value that is set in advance to determine whether or not abnormality is present. For example, in a case where the liquid surface of the waste liquid recovery bottle 52 is higher than the reference value, when performing the washing process, there is a possibility that the waste liquid may overflow from the waste liquid recovery bottle 52, and thus the controller determines that abnormality is present. In addition, in a case where the liquid surface of the wash buffer bottle 56 is lower than the reference value, there is a possibility that the wash buffer may be deficient during the washing process, and thus the controller determines that there is abnormality. In a case where it is determined that abnormality is present, the hybridization process is not initiated before the abnormality disappears.

On the other hand, in a case where it is determined that abnormality is not present (that is, the liquid surface of the waste liquid recovery bottle 52 is lower than the reference value, and the liquid surface of the wash buffer bottle 56 is higher than the reference value), the well cover 44 is rotated by the rotation mechanism of the well cover supporting mechanism 42, and the suction nozzle 46 and the injection nozzle 48 are moved to an upper side of any one of the wells 40. Next, the well cover 44 is downwardly moved by the linear motion mechanism of the well cover supporting mechanism 42 to bring the lower surface of the well cover 44 into contact with the upper surface of the well plate 38. According to this, the respective openings of the wells 40 are hermetically sealed by the well cover 44. In this state, temperature control with respect to the well plate 38 is performed by the temperature controller, and retention is performed for a predetermined time to perform the hybridization with respect to the microarray 1.

The washing process is performed after performing the hybridization process as described above. When the washing process is initiated, the well cover 44 is upwardly moved by the linear motion mechanism of the well cover supporting mechanism 42, and then the well cover 44 is rotated by the rotation mechanism to move the suction nozzle 46 and the injection nozzle 48 to an upper side of the well 40 to be washed. Next, the well cover 44 is downwardly moved by the linear motion mechanism of the well cover supporting mechanism 42. According to this, as illustrated in FIG. 14(*a*), the suction nozzle 46 and the injection nozzle 48 are inserted between the inner wall of the well 40 and the microarray holder 30 along the concave portion 40*a*. At this time, the suction nozzle 46 and the injection nozzle 48 descend in the well 40 along the concave portion 40*a* until each front end is located at a height position on a lower side of the lower end of the microarray 1 accommodated in the well 40.

Continuously, the suction pump 50 is operated to suction the liquid (the liquid sample or the wash buffer) from the well 40 by the suction nozzle 46. As described above, the suction nozzle 46 descends until the front end thereof is located at the height position on a lower side of the lower end of the microarray 1 accommodated in the well 40. Accordingly, as illustrated in FIG. 14(*b*), the liquid can be suctioned from the well 40 until the liquid surface in the well 40 is lowered to a height position on a lower side of the lower end of the microarray 1. The liquid that is suctioned by the suction nozzle 46 is conveyed to the waste liquid recovery bottle 52 through the suction pump 50.

Particularly, the well cover 44 is downwardly moved by the linear motion mechanism, and thus the liquid is suctioned from the well 40 by the suction nozzle 46 in combination with descending of the suction nozzle 46 and the injection nozzle 48 in the well 40. Accordingly, it is possible to shorten a time necessary for the washing process.

The liquid is suctioned from the well 40 until the liquid surface in the well 40 is lowered to a height position on a lower side of the lower end of the microarray 1, and then the injection pump 54 is allowed to operate so as to inject the cleansing liquid into the well 40 by the injection nozzle 48. At this time, the wash buffer is injected until the liquid surface in the well 40 reaches a height position on an upper side of the upper end of the microarray 1. In this manner, the liquid is suctioned to a height position on a lower side of the lower end of the microarray 1, and then the wash buffer is injected into the well 40. Accordingly, it is possible to sufficiently substitute the liquid in the well 40 and the wash buffer with each other, and thus it is possible sufficiently clean the microarray 1.

On the other hand, in a case where liquid leakage is detected by the liquid leakage sensor of the base 36, the injection of the wash buffer into the well 40 is stopped. According to this, even when the liquid is not normally suctioned from the well 40 due to abnormality in the suction pump 50 and the like, and thus the wash buffer that is injected into the well 40 overflows, it is possible to prevent further liquid leakage.

Next, the well cover 44 is upwardly moved by the linear motion mechanism of the well cover supporting mechanism 42, and then the well cover 44 is rotated by the rotation mechanism to upwardly move the suction nozzle 46 and the injection nozzle 48 to an upper side of the well 40 (for example, an adjacent well 40) to be subsequently washed. Continuously, the well cover 44 is downwardly moved by the linear motion mechanism of the well cover supporting mechanism 42, and then the suction nozzle 46 and the injection nozzle 48 are allowed to descend into the well 40 to be subsequently washed. Similarly, the respective processes relating to the descending of the suction nozzle 46 and the injection nozzle 48, the suction of the liquid, and the injection of the wash buffer are repeated for a predetermined number of times with respect to all of the wells 40 (although being different depending on experiment conditions and the like, for example, 30 times to 40 times).

After repeating the respective processes relating to the descending of the suction nozzle 46 and the injection nozzle 48, the suction of the liquid, and the injection of the wash buffer for a predetermined number of times with respect to all of the wells 40, temperature control is performed with respect to the well plate 38 by the temperature controller, and retention is performed for a predetermined time to perform drying of the microarray 1.

Finally, a modification example of the microarray processing apparatus 34, the well plate 38 of the microarray processing apparatus 34, the microarray holder 30, and the method of washing the microarray 1 will be described.

In the above-described embodiment, the microarray holder 30 pinches the outer edge of the flat plate-shaped microarray 1 from both sides of one main surface and the other main surface. However, a microarray and a microarray holder which have a different configuration may be used. For example, a frame-shaped microarray holder, which comes into close contact with a side end surface of the flat plate-shaped microarray to hold the microarray, may be used. In addition, one microarray holder may be configured to hold a plurality of microarrays.

In addition, in the above-described embodiment, a description has been made with respect to a case in which the well cover 44 is downwardly moved by the linear motion mechanism of the well cover supporting mechanism 42 to allow the suction nozzle 46 and the injection nozzle 48 to descend in the well 40 along the concave portion 40*a*. However, the well plate 38 may be upwardly moved by a predetermined linear motion mechanism to allow the suction nozzle 46 and the injection nozzle 48 to relatively descend with respect to the well 40.

In addition, FIG. 8 illustrates an example in which the lengths of the suction nozzle 46 and the injection nozzle 48 are approximately the same as each other has been exemplified. However, the suction nozzle 46 may descend until the front end thereof is located at a height position on a lower side of the lower end of the microarray 1 accommodated in the well 40, and the length of the injection nozzle 48 may be set to be shorter than the length of the suction nozzle 46.

In addition, FIG. 11 illustrates an example in which with regard to the inner length of the well 40, the inner length D1 of the well 40 in a range from a position on an upper side of the bottom surface of the well 40 by the length L4 to the opening of the well 40 is larger than the inner length D2 of the well 40 in a range from the bottom surface of the well 40 to a position on an upper side of the bottom surface by the length L4. However, the inner length of the well 40 from the bottom surface of the well 40 to the opening may be equal in each case. For example, the inner length from the bottom surface of the well 40 to the opening may be set to D2, and the gap between the inner wall of the well 40 and the microarray holder 30 may be set to be smaller than the outer diameter of the suction nozzle 46.

In addition, FIG. 11 illustrates an example in which the concave portion 40a having the approximately V-shaped cross-section is formed in a range from the bottom surface of the well 40 to a position on an upper side of the bottom surface by the length L4. However, a concave portion 40a, which has the same arc-shaped cross-section from the bottom surface of the well 40 to the opening, may be formed.

In addition, when performing the hybridization process and the washing process with respect to the microarray 1, an end scheduled time (time of day) of each process may be displayed. For example, operation conditions such as a reaction time in the hybridization process and the number of washing times in the washing process are input in advance by a known input means such as a touch panel and a numeric keypad. Then, a known calculator calculates an end scheduled time (time of day) on the basis of the operation conditions that are input, and a calculation result is displayed on a display.

Figure 15:
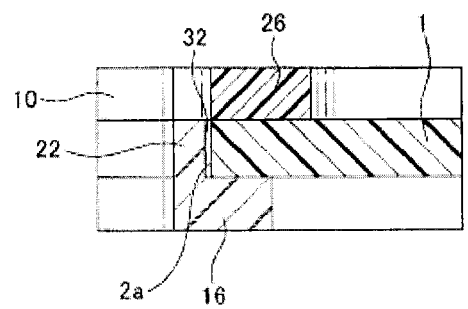
FIG. 15 is a partially enlarged cross-sectional view illustrating a modification example of the microarray holder according to the embodiment of the invention.

FIG. 15 is a partially enlarged cross-sectional view illustrating a modification example of the microarray holder 30 according to the embodiment of the invention.

FIG. 7 illustrates a case in which the groove 16 of the holder main body 10 and the cover member 26 pinch the outer edge of the microarray 1 at positions that are completely offset in the thickness direction of the microarray 1. However, as illustrated in FIG. 15, the groove 16 of the holder main body 10 and the cover member 26 may pinch the outer edge of the microarray 1 at positions that are at least partially offset in the thickness direction of the microarray 1. That is, a region in which the groove 16 of the holder main body 10 comes into contact with one main surface (lower surface in FIG. 15) of the microarray 1 and a region in which the cover member 26 comes into contact with the other main surface (upper surface in FIG. 15) of the microarray 1 may partially overlap with each other in the thickness direction of the microarray 1.

Even in this case, the gap 32 between the side end surface 2a of the microarray 1 and the holder main body 10 is not covered with the cover member 26, and thus the wash buffer can easily intrude into a space between the holder main body 10 and the side end surface 2a of the microarray 1. Accordingly, it is possible to reliably wash the liquid sample with the wash buffer.

The invention is not limited to the above-described embodiment, and various modification and changes may be made in a range of technical matters described in claims.

EXPLANATIONS OF LETTERS OR NUMERALS

1: Microarray
2: Microarray main body
2a: Side end surface
4: Through-hole
6: Through-hole forming portion
8: Cut-out portion
10: Holder main body
12: Cover member mounting portion
14: Pin hole
16: Groove
18: Opening
20: Protrusion
22: Guide
24: Concave portion
26: Cover member
28: Pin
30: Microarray holder
32: Gap
34: Microarray processing apparatus
36: Base
36a: Protrusion
38: Well plate
38a: Circular hole
40: Well
40a: Concave portion
42: Well cover supporting mechanism
44: Well cover
46: Suction nozzle
48: Injection nozzle
50: Suction pump
52: Waste liquid recovery bottle
54: Injection pump
56: Wash buffer bottle

The invention claimed is:

1. A microarray processing apparatus comprising:
a well plate in which at least one well is formed, each well accommodating a microarray which has a flat shape and whose outer edge is held by a microarray holder in an erected state to a bottom surface of each well, and having a concave portion formed at an inner wall of each well; and
a well cover which comes into contact with an upper surface of the well plate and hermetically seals an opened upper end of each well,
wherein the concave portion has an opened upper end, and extends along a depth direction of each well from the bottom surface to the opened end of each well, and
a length of the concave portion along the depth direction of each well is longer than a height of the microarray accommodated in each well and is longer than a height of the microarray holder accommodated in each well.

2. The microarray processing apparatus according to claim 1, further comprising:
a well cover supporting mechanism which supports the well cover in such a manner that a lower surface of the well cover faces the upper surface of the well plate above an upper side of the well plate, and which moves the well cover in a direction perpendicular to the upper surface of the well plate.

3. The microarray processing apparatus according to claim 2,
wherein the well plate has a circular plate shape,
a plurality of the wells are arranged in a circumferential direction of the circular plate shape of the well plate,
the well cover has a circular plate shape and has substantially the same external appearance as the well plate, and
the well cover supporting mechanism rotates the well cover around a central axis of the circular plate shape of the well cover.

4. The microarray processing apparatus according to claim 1, further comprising a suction nozzle that suctions a liquid from each well,
wherein a front end of the suction nozzle can be inserted into the concave portion up to a height position of a lower end of the microarray accommodated in each well, and
the suction nozzle is movable in each well along the depth direction until the front end of the suction nozzle is located at the height position of the lower end of the microarray accommodated in each well.

5. The microarray processing apparatus according to claim 4,
Wherein the suction nozzle is movable in each well along the depth direction until the front end of the suction nozzle is located at a height position spaced away from the bottom surface of each well by a distance ranging from 1 mm to 2 mm.

6. The microarray processing apparatus according to claim 4,
wherein a front end surface of the suction nozzle has an inclination angle of 10° or less with respect to the bottom surface of each well.

7. The microarray processing apparatus according to claim 4, further comprising:
an injection nozzle through which a liquid is injected into each well.

8. The microarray processing apparatus according to claim 7,
wherein the concave portion has a shape into which a front end of the injection nozzle can be inserted up to a height position lower than a position of an upper end of the microarray accommodated in each well, and
the injection nozzle is movable in each well along the depth direction until the front end of the injection nozzle is located at a height position lower than a position of the upper end of the microarray accommodated in the well.

9. The microarray processing apparatus according to claim 1, further comprising:
an input means for receiving an input of operation conditions relating to a hybridization process and a washing process,
a calculation means for calculating an end scheduled time of the hybridization process and the washing process based on the operation conditions that are input through the input means, and
an output means for outputting a calculation result obtained by the calculation means.

10. A method of washing a microarray, the method comprising:
accommodating the microarray in a well which is one of the at least one well of the microarray processing apparatus according to claim 1,
descending a suction nozzle in the well until a front end of the suction nozzle is located at a height position of a lower end of the microarray accommodated in the well;
suctioning a liquid from the well by the suction nozzle until a liquid surface in the well is lowered to a height position of the lower end of the microarray; and
injecting a wash buffer into the well by an injection nozzle after the suctioning.

11. The method of washing a microarray according to claim 10, wherein the descending, the suctioning, and the injecting are repeated a plurality of times.

12. The method of washing a microarray according to claim 10,
wherein the liquid is suctioned from the well by the suction nozzle while descending the suction nozzle in the well.

* * * * *